United States Patent
Guala

(10) Patent No.: US 6,641,559 B2
(45) Date of Patent: Nov. 4, 2003

(54) BURET WITH FOOT VALVE FOR MEDICAL INFUSION EQUIPMENT

(75) Inventor: Gianni Guala, Turin (IT)

(73) Assignee: Industrie Porla SPA, Turin (IT)

( * ) Notice: Subject to any disclaimer, the term of this patent is extended or adjusted under 35 U.S.C. 154(b) by 0 days.

(21) Appl. No.: 09/993,773

(22) Filed: Nov. 27, 2001

(65) Prior Publication Data

US 2002/0065491 A1 May 30, 2002

(30) Foreign Application Priority Data

Nov. 28, 2000 (IT) ..................................... TO2000A1111

(51) Int. Cl.[7] ................................................ A61M 1/00
(52) U.S. Cl. ....................... 604/127; 604/245; 604/247; 604/254
(58) Field of Search ................................. 604/127, 247, 604/254, 414, 245, 246, 251, 405, 411

(56) References Cited

U.S. PATENT DOCUMENTS

| 3,656,505 A | * | 4/1972 | O'Brian | 137/399 |
| 4,078,563 A | * | 3/1978 | Tuseth | 604/127 |
| 4,175,558 A | * | 11/1979 | Hess et al. | 604/127 |
| 5,423,346 A | * | 6/1995 | Daoud | 137/399 |
| 5,730,730 A | * | 3/1998 | Darling, Jr. | 604/246 |

* cited by examiner

Primary Examiner—Brian L. Casler
Assistant Examiner—Jeremy Thissell
(74) Attorney, Agent, or Firm—Sughrue Mion, PLLC

(57) ABSTRACT

A buret with foot valve for medical infusion equipment, including a transparent cylindrical container having a bottom wall with a central outlet hole for outlet of the liquid and a lateral graduated scale for indication of the level of the liquid. A float disk co-operates inside the container with the graduated scale for immediate identification of the level of the liquid, and a valve obturator is associated to the float disk for closing the outlet hole when the liquid inside the container comes to an end. The valve obturator is floating with respect to the float disk.

6 Claims, 2 Drawing Sheets

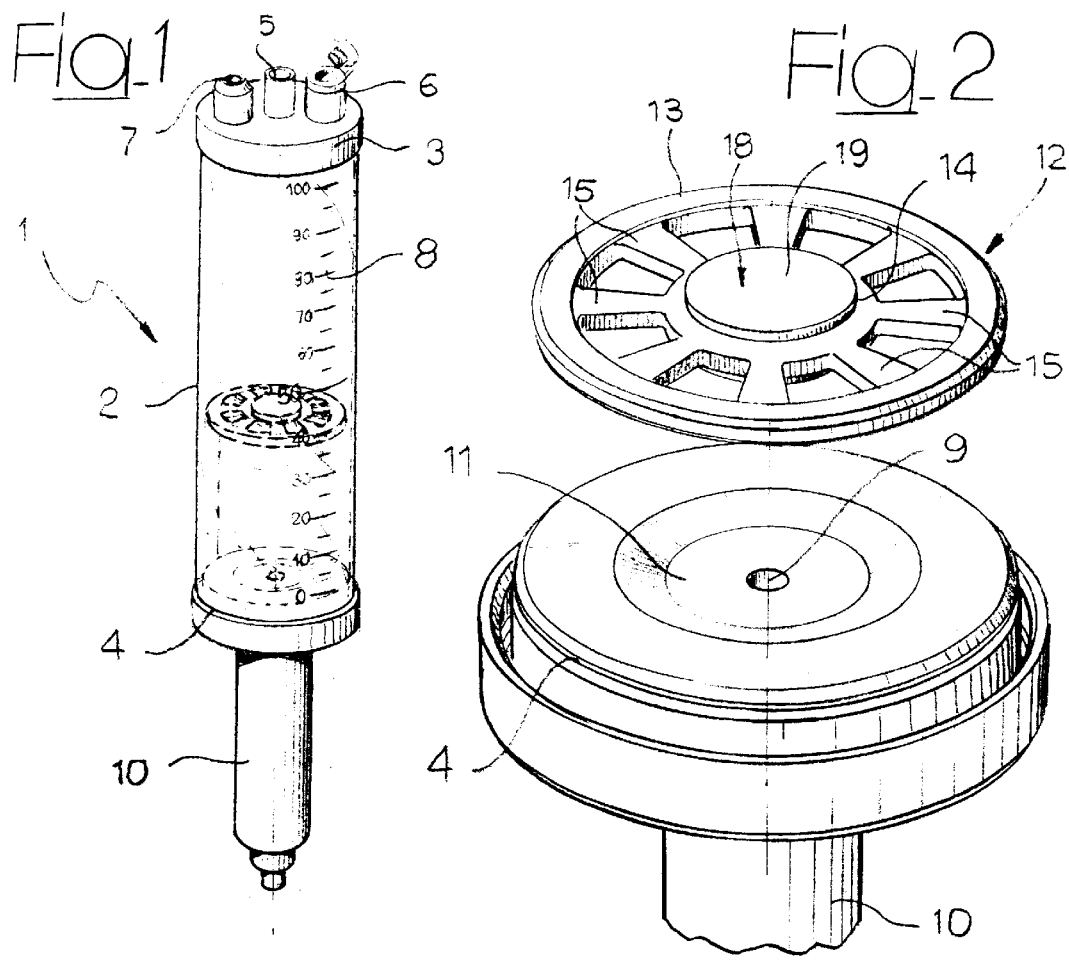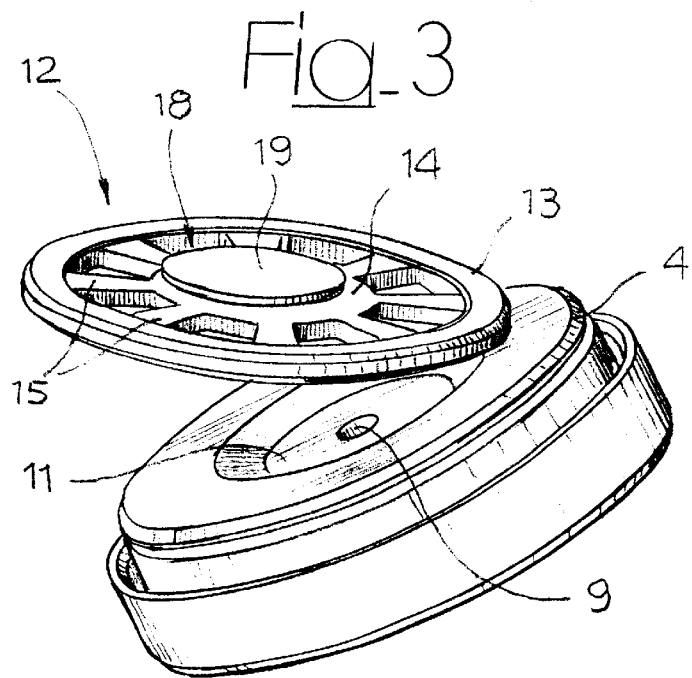

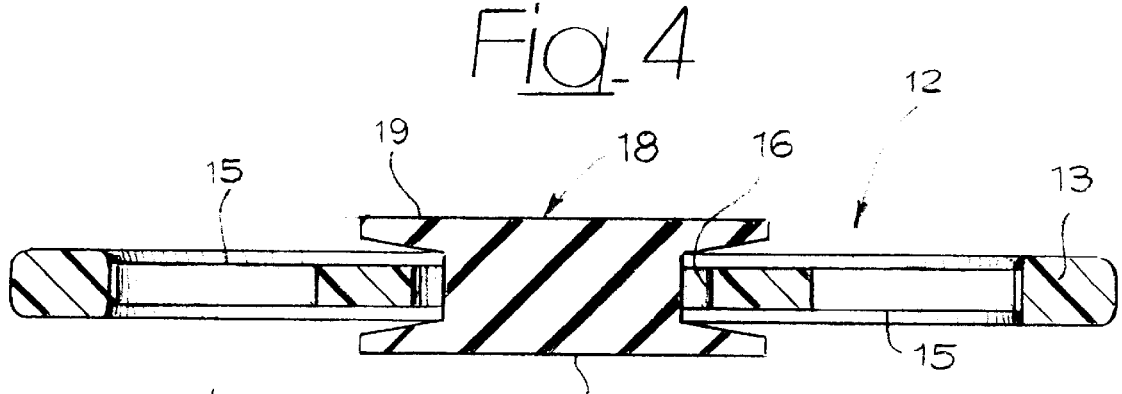
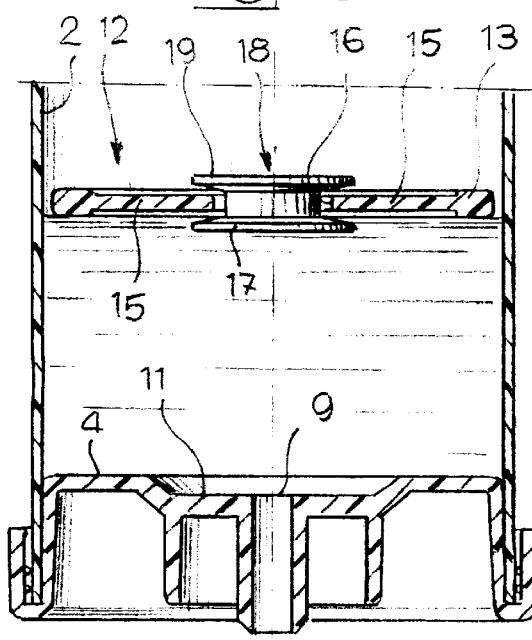
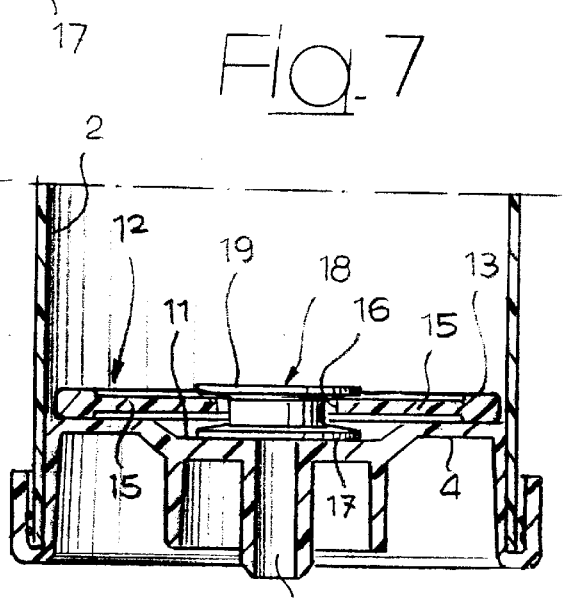
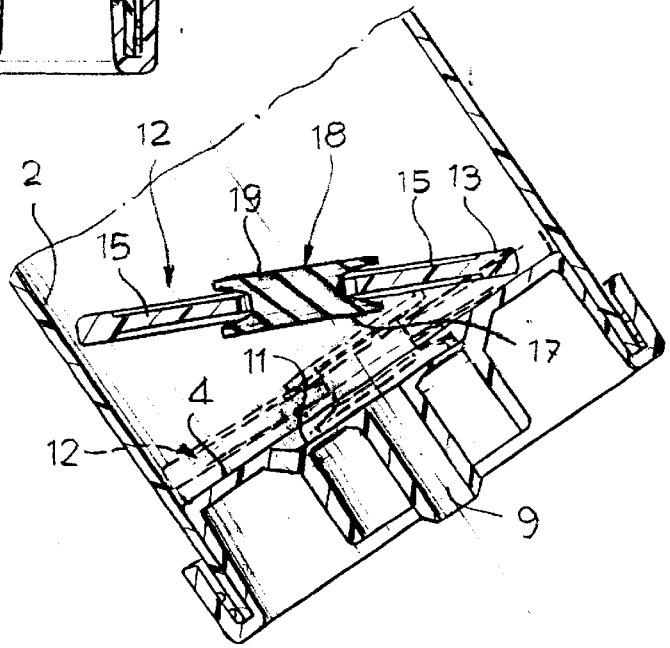

BURET WITH FOOT VALVE FOR MEDICAL INFUSION EQUIPMENT

BACKGROUND OF THE INVENTION

The present invention relates to burets with foot valves for medical infusion equipment.

Burets of the above type are generally known, for example, from the documents U.S. Pat. No. 4,175,558 (in which the foot valve includes a floating ball-type obturator) and U.S. Pat. No. 4,078,563 (in which the foot valve consists of a floating disk).

In greater detail, the invention relates to a buret of the type comprising an elongated transparent cylindrical container having a top inlet for the liquid, a bottom wall with a central hole for outlet of the liquid, a lateral graduated scale for indication of the level of the liquid inside the container, a float disk co-operating inside the container with the graduated scale for immediate identification of said level, and a valve obturator associated to the float disk for closing the outlet hole when, during use, the liquid inside the container comes to an end.

Burets of this type, which are currently manufactured and marketed by the present applicant, afford, thanks to integration between the floating indicator disk and the valve obturator, the advantage of a construction that is relatively simple, and hence more economical, as well as being of a high level of reliability and safety of operation as compared to solutions that envisage, for the floating indicator and the valve obturator, two distinct and independent elements. However, the aforesaid known burets, in which the obturator is formed by an element made of elastomeric material rigidly fixed to the float disk, are not always able to ensure proper closing of the outlet hole in the bottom wall of the container. In fact, closing is generally guaranteed when, during use, the buret is set in a perfectly vertical position, or else with just a small angle of inclination with respect to the vertical, When, instead, for any reason the inclination of the buret exceeds 10–15 degrees (in extreme cases up to 30 degrees), the float disk, which is kept horizontally on the surface of the liquid, may impinge on the inclined side wall of the buret or in any case also set itself in a more or less inclined position with respect to the bottom wall of the buret, so preventing the valve obturator from closing the outlet hole correctly when the liquid comes to an end. In the medical applications in question, the above drawback may entail even serious consequences for the patient who is connected to the buret.

SUMMARY OF THE INVENTION

The purpose of the present invention is to overcome the above drawback, and more in particular to provide a buret of the type defined above, shaped in such a way as to ensure in any operating condition, namely, even with major inclinations with respect to the vertical, correct, safe, reliable and complete closing of the foot valve when the liquid inside the container comes to an end.

According to the invention, the above purpose is achieved essentially thanks to the fact that the aforesaid valve obturator is made of a soft elastic material and is floating with respect to the float disk.

In greater detail, the float disk has a central opening through which there is inserted, with axial and radial play, a generally cylindrical body made of elastic material which has two end radial flanges facing on opposite sides said opening, one of the said flanges constituting said valve obturator.

The valve obturator and the float disk may be of equal, or more conveniently different, absolute gravity.

According to another aspect of the invention, the bottom wall of the container defines, around the aforesaid outlet hole, a sump designed to house said obturator when the float disk rests against said bottom wall.

BRIEF DESCRIPTION OF THE DRAWINGS

Further characteristics of the invention will emerge clearly from the ensuing detailed description with reference to the attached drawings, which are provided purely by way of non-limiting example and in which:

FIG. 1 is a schematic perspective view illustrating a buret for medical infusion equipment according to the present invention;

FIG. 2 is an exploded perspective view at a larger scale of the foot valve of the buret, represented in the condition of use corresponding to FIG. 5;

FIG. 3 is a view similar to that of FIG. 2, with the foot valve represented in the condition of use corresponding to FIG. 6;

FIG. 4 is a transverse cross-sectional view at a larger scale of the float disk—obturator assembly of the buret;

FIG. 5 is a partial axial cross-sectional view, at a larger scale than FIG. 1, of the foot valve in the open condition, corresponding to the one represented in FIG. 2;

FIG. 6 is a view similar to that of FIG. 5, illustrating the foot valve in an initial closing phase, corresponding to FIG. 3; and FIG. 7 is a view similar to those of FIGS. 5 and 6, showing the foot valve in the closed condition.

DETAILED DESCRIPTION OF THE INVENTION

With reference to the drawings, numeral 1 designates, as a whole, a buret for medical intravenous infusion equipment, basically comprising an axially elongated transparent cylindrical container 2 having a lid 3 at the top and a bottom wall designated as 4 at the bottom. The lid 3 is provided, in a way generally in itself known, with a central tubular connector 5 for connection to a hose for supplying an infusion liquid, an air inlet with a filter 6, and an injection site 7 for possible introduction of additional substances by means of a syringe.

The transparent container 2 is provided laterally with a graduated vertical scale 8 for indication of the level of the liquid inside the container.

The bottom wall 4 has, at its centre, a hole 9 for outlet of the liquid, communicating, in a way in itself known, with a dripping chamber 10 fixed to the buret and designed to be connected to the patient.

According to one of the characteristics of the invention, around the outlet opening 9 the bottom wall 4 is formed with a sunken part 11, which constitutes a sump. As it can be be seen, the bottom of the sump 11 that surrounds the outlet opening 9 defines the annular seat for a foot valve with which the buret 1 is equipped.

The reference number 12 designates a float disk inserted, with radial play, inside the container 1 and having the function of indicator co-operating with the graduated scale 8 for immediate identification of the level of the liquid inside the container 2. In order to render indication of the level even more immediate, the float disk 12 may conveniently be of a bright colour, for instance red.

The said float disk 12 is made of a single piece of moulded rigid plastic material and consists of an outer ring 13 and an inner ring 14 which are connected together by radial arms 15 set at distances apart.

According to the basic characteristic of the invention, inserted in a floating way in the central opening 16 defined by the inner ring 14 is the foot valve obturator of the buret 1. The said obturator practically consists of a radial flange of the bottom end 17 of a generally cylindrical body 18 made of a soft elastic and anti-allergic material, for example silicone or thermoplastic rubber, such as polyisoprene. The body 18 is inserted, with axial and radial play, through the central opening 16 of the float disk 12 and has at its top end a radial flange 19 similar to the bottom flange 17.

The outer diameter of the bottom flange 17, which, as has been said, constitutes the foot-valve obturator, is smaller than that of the sump 11 of the bottom wall 4.

The valve obturator 17 and the float disk 12 may be of equal, or more conveniently different, absolute gravity.

FIGS. 5, 6 and 7 show, by way of example, operation of the foot valve, and in particular of the obturator 17.

In the presence of liquid inside the container 2 of the buret 1, the float disk 12 with the body 18 floats on the surface of the liquid, dropping progressively towards the bottom wall 4 as the liquid comes out through the opening 9 (FIG. 5). In the case where the buret 1 is set basically vertical, when the liquid comes to an end, the float disk 12 sets itself with its outer ring 13 resting against the bottom wall 4, and the obturator 17 sets itself against the bottom of the sump 11, thus interrupting the communication between the opening 9 and the inside of the container 2 (FIG. 7). The presence of the sump 11 prevents large residual amounts of liquid from remaining on the bottom of the container 1 upon closing of the foot valve.

In the case, instead, where the buret 1 is inclined with respect to the vertical, even at a large angle in the region of 25°, as illustrated in FIG. 6, closing of the foot valve is in any case guaranteed in a reliable and secure way thanks to the floating arrangement of the body 18 with the obturator 17. In the said eventuality, in fact, first the outer ring 13 of the float disk 12 will rest on one side against the bottom wall 4 and then gradually, during outflow of the residual liquid, will position itself parallel to said bottom wall 4, while the obturator 17 will set itself on the bottom of the sump 11, thus closing the opening 9, in the way represented by a dashed line in FIG. 6.

It should be noted that the float disk 12/body 18 assembly with the obturator 17 is altogether symmetrical, a fact that facilitates assembling of the buret 1 since insertion of the assembly inside the container 2 does not require any particular orientation of the latter.

Of course, the details of construction and the embodiments may vary widely with respect to what is described and illustrated herein, without thereby departing from the scope of the present invention as defined in the ensuing claims.

What is claimed is:

1. A buret with foot valve for medical infusion equipment, including an elongated transparent cylindrical container having a top inlet hole for the inlet of a liquid, a bottom wall with a central outlet hole for the outlet of said liquid, a lateral graduated scale for indication of the level of said liquid inside said container, a float disk co-operating inside said container with said graduated scale for immediate identification of said level of the liquid, and a valve obturator associated to said float disk for closing said outlet hole when, in use, the liquid inside said container comes to an end, said valve obturator being made of soft elastic material and being floating with respect to said float disk.

2. The buret according to claim 1, wherein said float disk has a central opening through which there is inserted, with axial and radial play, a generally cylindrical body made of elastic material, said body having two end radial flanges facing on opposite sides said opening, one of the said flanges constituting said valve obturator.

3. The buret according to claim 1, wherein said valve obturator and said float disk are of equal absolute gravity.

4. The buret according to claim 1, wherein said valve obturator and said float disk are of different absolute gravity.

5. The buret according to claim 1, wherein said bottom wall of said container defines, around the said outlet hole, a sump designed to house said obturator when said float disk rests against said bottom wall.

6. The buret according to claim 1, wherein said float disk comprises an outer ring and an inner ring defining said central opening, and radial arms set at distances apart that connect said outer ring and inner ring together.

* * * * *